United States Patent
Houghton et al.

[11] Patent Number: 6,139,538
[45] Date of Patent: Oct. 31, 2000

[54] IONTOPHORETIC AGENT DELIVERY TO THE FEMALE REPRODUCTIVE TRACT

[75] Inventors: William C. Houghton, St. Paul, Minn.; Keith R. Hildebrand, Houlton, Wis.; Martin B. Finkelstein, St. Paul, Minn.; Frederick J. Foley, Bedford, N.H.

[73] Assignee: Iotek, Inc., Minneapolis, Minn.

[21] Appl. No.: 08/943,966

[22] Filed: Oct. 6, 1997

[51] Int. Cl.[7] ............................. A61M 31/00; A61N 1/30
[52] U.S. Cl. ................................ 604/515; 604/21
[58] Field of Search ...................... 604/11, 21, 54, 604/55, 193, 275, 278, 279, 19, 20, 27, 39–41, 93, 117, 501, 514, 515; 606/41; 607/39, 115, 116, 138

[56] References Cited

U.S. PATENT DOCUMENTS

| | | | |
|---|---|---|---|
| 487,655 | 12/1892 | Wardell | 604/20 |
| 1,030,543 | 6/1912 | Saunders | 604/21 |
| 1,652,327 | 12/1927 | Richter | 604/41 |
| 1,740,240 | 12/1929 | Honey . | |
| 1,776,357 | 9/1930 | Hart . | |
| 2,361,908 | 11/1944 | Bayers | 604/41 |
| 3,422,814 | 1/1969 | Lloyd . | |
| 3,721,229 | 3/1973 | Panzer . | |
| 4,335,719 | 6/1982 | Johnson | 604/41 |
| 4,601,698 | 7/1986 | Moulding, Jr. | 604/22 |
| 5,209,754 | 5/1993 | Ahluwalia | 606/119 |
| 5,232,441 | 8/1993 | Stephen et al. | 604/49 |
| 5,242,390 | 9/1993 | Goldrath | 604/21 |
| 5,248,304 | 9/1993 | Vigdorchik et al. | 604/41 |
| 5,352,192 | 10/1994 | Byrne et al. | 604/21 |
| 5,486,160 | 1/1996 | Rossi et al. | 604/21 |
| 5,720,717 | 2/1998 | D'Andrea | 604/21 |
| 5,749,845 | 5/1998 | Hildebrand et al. | 604/21 |
| 5,769,880 | 6/1998 | Truckai et al. | 604/20 |

FOREIGN PATENT DOCUMENTS

| | | |
|---|---|---|
| 0 018 097 A2 | 10/1980 | European Pat. Off. . |
| 0 438 078 A2 | 7/1991 | European Pat. Off. . |
| 0 510 857 A1 | 10/1992 | European Pat. Off. . |
| 2 090 535 | 7/1982 | United Kingdom . |

*Primary Examiner*—Sharon Kennedy
*Attorney, Agent, or Firm*—Merchant & Gould P.C.

[57] ABSTRACT

An apparatus for iontophoretically delivering an agent to a patient having a uterus and a cervix. The apparatus comprises a probe sized to fit within the cervical canal. A cervical cap has an inner surface. The probe projects from the inner surface. A first electrode has a first portion operably connected to the cervical cap and a second portion operably connected to the probe. The first electrode is configured to be electrically connected to a power supply. A second electrode is configured to be electrically connected to the power supply. A reservoir having a first portion operably connected to the cervical cap and a second portion operably connected to the probe.

14 Claims, 8 Drawing Sheets

IONTOPHORETIC AGENT DELIVERY TO THE FEMALE REPRODUCTIVE TRACT

TECHNICAL FIELD

This invention generally relates to iontophoretic delivery of an agent to bodily tissue, and more particularly, to iontophoretic delivery of an agent to the female reproductive tract.

BACKGROUND

Systemic delivery has many shortcomings. When administered at higher levels and exposed to otherwise healthy tissue, such agents may harm healthy tissue and cause serious side effects. Furthermore, many agents are expensive. When these agents are delivered systemically, a caregiver must administer a higher dose in order to achieve a higher level of agent at the site of diseased tissue. As a result, much of the drug is wasted, which drives up the cost of the treatment. This waste is very significant given the high cost of pharmaceuticals.

Because of these shortcomings of systemic delivery, it is advantageous to preferentially treat the affected area. Many caregivers inject the agent directly to target tissue to preferentially treat an area of a patient's body. Internal delivery using injection requires penetration by a needle or similar device. Such penetration is intrusive, painful, often inaccurate, and does not evenly distribute the agent throughout the target area. To aggravate this situation, several injections may be required for relatively large target areas.

Transcutaneous delivery is one current technique to minimize systemic distribution of the agent. However, such delivery systems are limited to the application of an agent through the patient's skin or other surface tissue. Thus, transcutaneous delivery of an agent is inefficient especially if the target area is large and/or deep within the patient's body such as cervical and uterine tissue. Typically an amount of agent much larger than that required at the target site must be applied, which results in waste and is expensive.

The female reproductive tract is an example of a localized area within a women's body that is often treated by the systemic delivery of an agent or by direct injection of an agent. It is important to treat maladies that affect the reproductive tract, especially because there are many disorders that can threaten the life of a woman if not treated in their early stages. An example of such a disorder is human papillomavirus, which is a virus that can cause dysplasia and precursor changes to cervical malignancy, the second most common cancer in women. The longer these conditions go untreated, the more difficult they are to cure. As the disease progresses, it may need to be treated with major reconstructive surgery, increasingly dangerous agents such as cytotoxic agents or chemotherapeutic agents, and/or radiotherapy.

In addition to the delivery of an agent, a caregiver frequently needs to perform diagnostic or therapeutic procedures directly to the reproductive tract in order to effectively treat a patient. Examples of such procedures include hysteroscopy, tissue biopsy, and endometrial ablation. These procedures are presently done with general or regional anesthesia (e.g., epidural and spinal), both of which expose the patient to significant risks. Paracervical nerve blocks are also widely used for minor diagnostic procedures. The difficulty is that such nerve blocks expose the patient to the pain and trauma of needle injections. Furthermore, even if performed perfectly, paracervical nerve blocks do not result in adequate anesthesia of the fundus of the uterus. Moreover, nerve blocks do not prevent cramping pains induced by a foreign body in the uterus.

Therefore, a need exists for an agent delivery apparatus that provides uniform distribution of the agent to a localized area of internal bodily tissue. More particularly, a need exists for an apparatus that can deliver an agent to the reproductive tract without systemic administration of the agent and without the use of an injection directly into the tissue. There is also a need for a delivery device and method of anesthetizing tissue in the reproductive tract without using a general anesthetic or regional/local anesthesia. There is yet another need for the treatment of human papillomavirus in which an agent can be delivered deep into the basal cell layer of the cervical epithelium.

SUMMARY

The present invention is directed to an apparatus for delivering an agent to a patient having a cervix. The apparatus comprises a probe sized to fit within the cervical canal. A cervical cap has an inner surface. The probe extends from the inner surface. A reservoir has first and second portions. The first portion is operably connected to the inner surface of the cap, and the second portion is operably connected to the probe. An alternative embodiment also has means for transporting agent from the first and second portions of the reservoir to cervical tissue.

Another embodiment of the present invention is directed to an apparatus for iontophoretically delivering an agent to a patient having a uterus and a cervix. The apparatus comprises a probe sized to fit within the cervical canal. An occlusion member is operably connected to the probe. The occlusion member is configured to substantially block the patient's cervical canal. First and second electrodes are configured to be electrically connected to a power supply. The first electrode is operable connected to the probe. A reservoir is positioned between the first and second electrodes.

Yet another embodiment of the present invention is directed to an apparatus for iontophoretically delivering an agent to a patient having a uterus and a cervix. The apparatus comprises a probe sized to fit within the cervical canal. A cervical cap has an inner surface. The probe projects from the inner surface. A first electrode has a first portion operably connected to the cervical cap and a second portion operably connected to the probe. The first electrode is configured to be electrically connected to a power supply. A second electrode is configured to be electrically connected to the power supply. A reservoir having a first portion operably connected to the cervical cap and a second portion operably connected to the probe.

Another embodiment of the present invention comprises an elongated member having a uterine delivery zone. the elongated member defines a uterine delivery lumen that is in fluid communication with the uterine delivery zone. An occlusion member is operably connected to the elongated member. The occlusion member is configured and arranged to engage the cervix and occlude the cervical canal. The uterine delivery zone is positioned within the uterine cavity when the occlusion member enagages the cervix.

Another embodiment of the apparatus comprises an elongated member configured to be inserted through the cervical canal. A compressible member is operably connected to the elongated member. A jacket is removably engaging and compressing the compressible member.

A method for delivering an agent to a patient having a uterus and a cervix comprises the steps of: positioning a reservoir adjacent to the cervix; positioning a first electrode adjacent to the reservoir and the cervix; positioning a second electrode in electrical communication with the patient's body; and applying a voltage gradient between the first and second electrodes, thereby transporting the agent from the reservoir to the cervical tissue.

An alternative method comprises the steps of: positioning a first electrode within the uterine cavity; positioning a second electrode into electrical communication with patient's body; delivering an agent into the uterine cavity; and applying a voltage gradient between the first and second electrodes, thereby transporting the agent from the uterine cavity to tissue in the uterine wall.

DETAILED DESCRIPTION

A preferred embodiment of the invention will be described in detail with reference to the drawings, wherein like reference numerals represent like parts and assemblies throughout the several views. Reference to the preferred embodiment does not limit the scope of the invention, which is limited only by the scope of the claims attached hereto.

In general, the present invention relates to the direct and even distribution of an agent to a localized area of the reproductive tract such as the cervix, uterine wall, or fallopian tubes. One possible embodiment of the present invention provides delivery of the agent directly into the cervix by delivering the agent directly into both the exocervix and/or the endocervix. The exocervix is the portion of the cervix that protrudes into the vagina and is lined with stratified squamous epithelium. The endocervix is the portion of the cervix that opens in the uterus and is also lined with stratified squamous epithelium. Another possible embodiment of the present invention provides delivery of the agent directly into the uterine wall. Yet another possible embodiment provides both simultaneous and direct delivery of an agent into both the cervix and uterine wall.

The present invention has many advantages. One advantage is that it permits a caregiver to isolate and target specific tissue within the reproductive tract for delivery of an agent. At the same time, the caregiver can minimize the exposure of other organ systems to the therapeutic agent. These advantages are very important when administering toxic or otherwise dangerous drugs that might cause serious side effects.

The present invention provides other advantages as well. The active iontophoretic drug delivery process serves to drive the agent deeper into, and more evenly throughout, the target tissue. This distribution of the agent is advantageous in achieving greater efficacy and increasing the duration of the desired effect. For example, when lidocaine is delivered for local anesthesia, iontophoretic delivery deep into the tissue will provide better anesthesia than previously available by passive delivery systems. Another advantage is that the caregiver can control the rate at which the agent is delivered by adjusting the current level used for iontophoresis.

Several possible embodiments of the present invention utilize iontophoresis as a transport mechanism for the agent. Iontophoresis is a method of active delivery of an ionic therapeutic agent into the body. In iontophoresis, an agent reservoir and a delivery electrode is positioned adjacent to the targeted tissue. A return electrode is also placed in electrical communication with the patient's body. More specifically, the return electrode is typically positioned on the surface of the patient's skin or is located on the delivery device itself. Depending on the embodiment of the invention that is used, the caregiver can load the reservoir with agent either before or after the delivery device is introduced into the patient and positioned for delivery.

A voltage gradient is then created between the delivery and return electrodes, which creates an electrical current. This electrical energy transports the agent from the reservoir into the target area. The agent is electrically charged. If the agent is inherently neutral, it is associated with a charged carrier molecule to facilitate iontophoretic delivery.

Alternatively, delivery can rely on electroosmosis if the agent is neither charged nor combined with a carrier molecule. Electroosmosis is a type of electrically assisted agent delivery in which small cations such as $Na^+$ are actively driven into the target tissue. In turn, aqueous solution is transported along with the $Na^+$ as part of the ionic hydration shell and as a result of the Na-based osmotic gradient. Nonionic solutes or particles are carried along with the aqueous solvent.

An agent can include any type of composition. Examples include drugs; compositions useful for diagnostic purposes such as dyes; fixatives; genetic material such as DNA, RNA, genes, antisense oligonucleotides, and other antisense material; local anesthetics such as lidocaine, carbocaine, bupivacaine, and ropivacaine; therapeutic agents such as cytotoxic, chemotherapeutic, photosensitive agents, antiviral agents; adjuvents; penetration enhancers; and other substances that have medical applications. Additionally, the term agent can mean an agent in the form of a solution, gel, liquid, or liposome. Although the term is often used in a singular form, it can connote either a single agent or a combination of agents.

Figure 1:
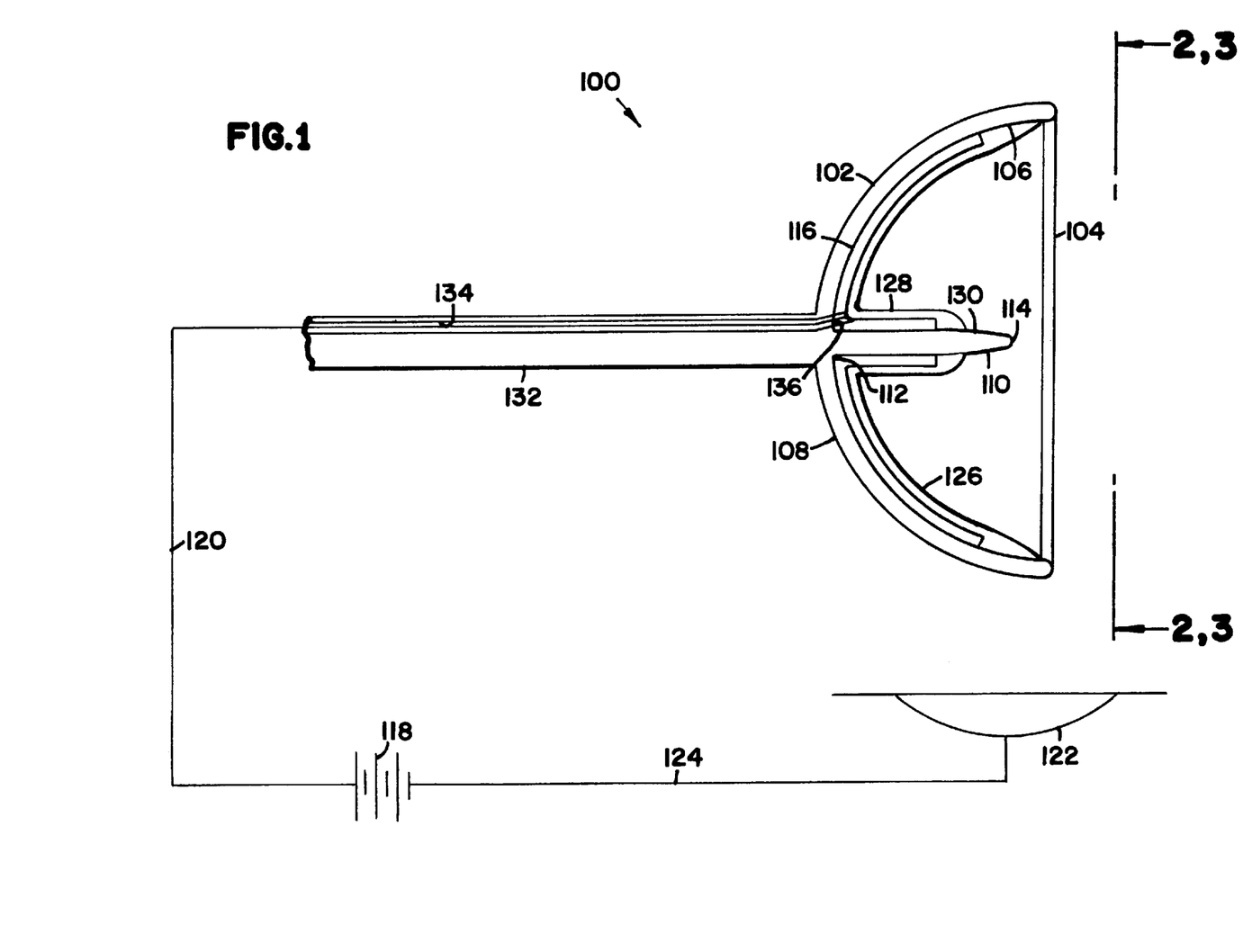
FIG. 1 is a fragmentary, cross-sectional view of an agent-delivery device that embodies the present invention.
Figure 2:
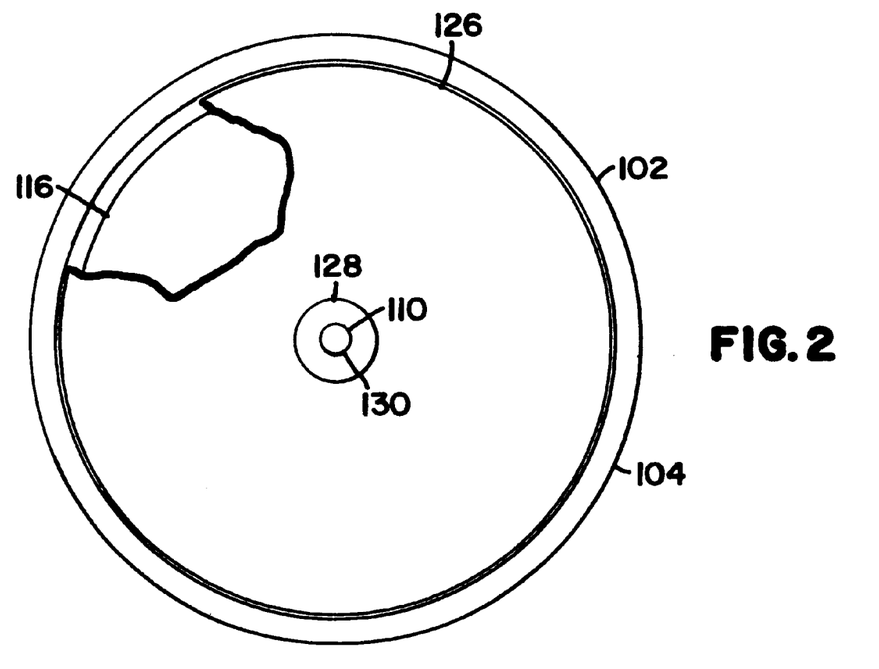
FIG. 2 is a fragmentary, side view of the agent-delivery device shown in FIG. 1 taken along line 2-2.

Referring now to FIGS. 1 and 2, an agent-delivery device, generally shown as 100, is configured for delivering an agent to a patient's cervix. The agent-delivery device 100 has a cap 102, which is a closely-fitting overlaying or covering structure. The cap 102 is generally configured to conform to the vaginal surface of a woman's cervix. The conforming nature of the cap 102 ensures a substantially even and uniform fit between the vaginal surface of the cervix and the cap 102, which promotes agent retention within the targeted area. In one possible configuration, the cap 102 is approximately the size and shape of a contraceptive diaphragm. The cap 102 is made of a biologically compatible material such as polyethylene, polyurethane, or silicone.

The cap 102 has a rim 104, an inner surface 106 and an outer surface 108. A probe 110 is operably connected to the cap 102 and projects outward from the inner surface 106. The probe 110 has a base 112 and a distal tip 114. The probe 110 is sufficiently rigid so that it does not collapse or bend back on itself when inserted into the cervical canal. Examples of material that can be used to form the probe 110 includes polyethylene and polyurethane.

A delivery electrode 116 is mounted on or operably connected to the inner surface 106 of the cap 102 and the surface of the probe 110. In one possible embodiment, the delivery electrode 116 covers substantially all of the inner surface 106 of the cap 102 and also extends along at least a portion of the probe 110. This embodiment promotes a uniform distribution of the agent throughout the cervix including both the endocervix and exocervix.

In one possible configuration, the delivery electrode 116 is formed with an electrically conductive coating such as a metal. In other possible configurations, the delivery electrode 116 is formed from strips of conductive material or a wire that is coiled around the probe 110 and then spirals along the inner surface 106 of the cap 102 starting at the base 112 of the probe 110 and working its way toward the rim 104 of the cap 102. A further alternative is a mesh configuration.

Yet another configuration has separate delivery electrodes, one mounted on the probe 110 and another mounted on the inner surface 106 of the cap 102. The delivery electrode 116 is electrically connected to an external power source 118 via a lead 120. If there are separate delivery electrodes, both electrodes are electrically connected to the power supply 118 to have the same polarity. In one possible configuration, the power supply can control each delivery electrode independently. This configuration is advantageous because it may require a greater amount to deliver a prescribed dose of agent through the stratified squamous epithelium that lines the cervix than the endometrium that lines the uterus.

A return electrode 122 is electrically connected to the power supply 118 via a lead 124. In one possible embodiment, the return electrode 122 is a patch-type electrode configured to be placed against the patient's skin.

The delivery and return electrodes 116 and 122 can be formed from an electrically conductive material. The material can be either sacrificial or non-sacrificial. Examples of sacrificial materials include silver/silver chloride, copper, tin, nickel, iron, lithium, and amalgams thereof. Examples of non-sacrificial materials include carbon, platinum, gold, and other noble metals. The electrodes 116 and 122 also can be formed from zirconium, iridium, titanium, and stainless steel, some of which may be subject to oxidation or reduction under certain circumstances.

A reservoir 126 is operably connected to the inner surface 106 of the cap 102. The reservoir 126 extends from a position proximate the rim 104 of the cap 102, to the base 112 of the probe 110 and outward along at least a portion of the probe 110. In this configuration, the reservoir 126 substantially covers the delivery electrode 116.

The reservoir 126 is formed from a material that is configured to retain an agent. Examples of agent-retaining materials include polymer matrices, open-cell foams, hydrogels, gels, creams, and cotton fiber. Examples of material that can be used to form a polymer matrix include polyactide, polyalkylcyanoacrylates, polyorthoesters and polyanhydrides. Examples of material that can be used to form an open-cell foam include polyurethane and cellulose. Examples of material that can be used to form a hydrogel include agarose, agar, and polyacrylamide. The reservoir 126 has a thickness of about 0.1 cm to about 0.5 cm.

This configuration has several advantages. For example, the reservoir 126 both holds the agent and provides an interface between the delivery electrode 116 and the cervix, which is the targeted bodily tissue. The reservoir 126 prevents direct contact between the delivery electrode 116 and the patient's tissue. This isolation minimizes the risk of hot spots, which are caused by shunting of the electrical current. The shunting of electrical current results in a high current density in a limited area that may result in pain, burning tissue, and an uneven distribution of the agent.

Another advantage is that the agent-retaining material maintains uniform contact with the bodily tissue. The reservoir 126 is made of material that is malleable or pliable enough to conform to the surface of the bodily tissue thereby creating uniform contact. Such uniform contact ensures a uniform distribution of current, which also minimizes the risk of hot spots and promotes an even distribution of the agent.

The probe 110 has a delivery portion 128, which is that portion of the probe 110 along which the reservoir 126 extends. The reservoir 126 covers the portion of the delivery electrode 116 that extends along the probe 110. The probe 10 has an introducer portion 130 between the distal tip 114 and the delivery portion 128. In one possible configuration, the introducer portion 130 is tapered toward the distal tip 114 to ease introduction of the probe 110 into the cervical canal. In an alternative embodiment, the reservoir 126 extends to the distal tip 114 of the probe 110.

The length of the probe 110 is set so that the tip 114 will remain in the cervical canal and will not substantially extend into the patient's uterus when the cap 102 is properly positioned against the cervix. In one possible embodiment, the length of the probe 110 from the base 112 to the distal tip 114 is in the range from about 1 cm to about 5 cm. In one possible configuration, the length of the introducer portion 130 of the probe 110 is about 1.5 cm. In other possible configurations, the length of the introducer portion 130 of the probe 110 is in the range from about 1 cm to about 2 cm.

The overall diameter of the probe 110, including that portion of the reservoir 126 that extends along the probe 110, is set so that the probe 110 will transverse the cervical canal so that there is uniform contact between the probe 110 and cervical tissue. At the same time, the probe 110 should not substantially dilate the cervical tissue to the extent that it causes trauma, causes discomfort, or induces contractions. In one possible configuration, the diameter of the probe 110 is between about 2 mm and about 5 mm.

The cap 102 and probe 110 can be sized to fit a cervix having an average size. Alternatively, the caregiver can keep a variety of drug-delivery devices 100 that have different sizes of caps 102 and/or probes 110. Additionally, dimensions provided herein for the description of this embodiment, as well as other embodiments, are only for purposes of example and do not limit the scope of the claimed invention. For example, the probe 110 may have a length that causes it to extend beyond the cervical canal and into the neck of the uterus or into the uterine cavity itself. Additionally, the probe 110 may have a diameter wide enough to dilate the cervical canal, which may be advantageous to remove folds of tissue along the cervical canal.

An elongated body 132 extends from the outer surface 108 of the cap 102. The elongated body 132 defines a delivery lumen 134. Additionally, the cap 102 and elongated body 132 define a delivery port 136 that provides fluid communication between the reservoir 126 and the delivery lumen 134. An alternative configuration includes multiple delivery ports located in various positions around the probe 110, which promotes a uniform distribution of the agent in the reservoir 126. The lead 120 extends through the delivery lumen 134. The elongated body 132 can have various angular orientations relative to the cap 102 in order to provide ease in introducing the agent-delivery device 100 and engaging the patient's cervix with the cap 102 and the probe 110.

In use, the caregiver inserts the agent-delivery device 100 through the patient's vaginal canal and positions the cap 102 over the vaginal surface of the patient's cervix and the probe 110 within the cervical canal. The caregiver then injects agent through the delivery lumen 134 until the reservoir 126 is loaded with the agent. Loading the reservoir 126 after the agent-delivery device 100 is positioned prevents premature loss of the agent as the cap 102, and hence the reservoir 126, is squeezed, bent, and folded while passing through the vaginal canal. As a result, exposure of the agent to healthy tissue and the circulatory system is minimized. Waste of the agent is also minimized.

An electric current is passed between the delivery and return electrodes 116 and 122, which causes the agent to be iontophoretically transported from the reservoir 120 into the patient's cervical tissue. Using iontophoresis to deliver the agent promotes substantially uniform distribution of the agent throughout the cervix, including both the endocervix and exocervix. The amount of current that is conducted between the delivery and return electrodes 116 and 122 and the duration of the delivery depends on several factors including the prescribed dose of agent, the patient's threshold level of electrically-evoked discomfort, and local tissue irritation. Additionally, the electrical current can be gradually increased or ramped up, which minimizes the sensation and discomfort felt by the patient. In other possible configurations, various DC waveforms can be used for the electric current. Although iontophoresis is the primary transport mechanism, a certain amount of agent will be passively absorbed into the cervical tissue.

Alternatively, the reservoir 126 is loaded with agent before the agent-delivery device 100 is inserted into the vaginal canal. In this alternative method, the cap 102 is dipped into the agent, which will be absorbed into the reservoir 126. If this alternative method of loading the agent is used, the delivery lumen 134 is not required. Another possible technique for loading the reservoir 126 is to hold the agent-delivery device 100 so that the inner surface 106 is pointed upward and fill the cap 102 with agent, which will become absorbed by the reservoir 126. An advantage of this technique is that air contained within the open-cell foam is displaced with agent before the device 100 is inserted. Air trapped in the foam or between the cap 102 and cervix may interfere with uniform iontophoretic delivery of the agent. Yet another possible techniques to load the reservoir 126 is to mix the agent into the material when the reservoir 126 is formed. This technique works especially well with gels and hydrogels.

An alternative embodiment of the agent-delivery device 100 does not include the elongated body 132. This alternate embodiment is introduced into the vaginal canal and positioned to engage the cervix in a manner similar to a contraceptive diaphragm. When using this alternative embodiment, the reservoir 126 is loaded with agent before the device is introduced into the vaginal canal.

Figure 3:
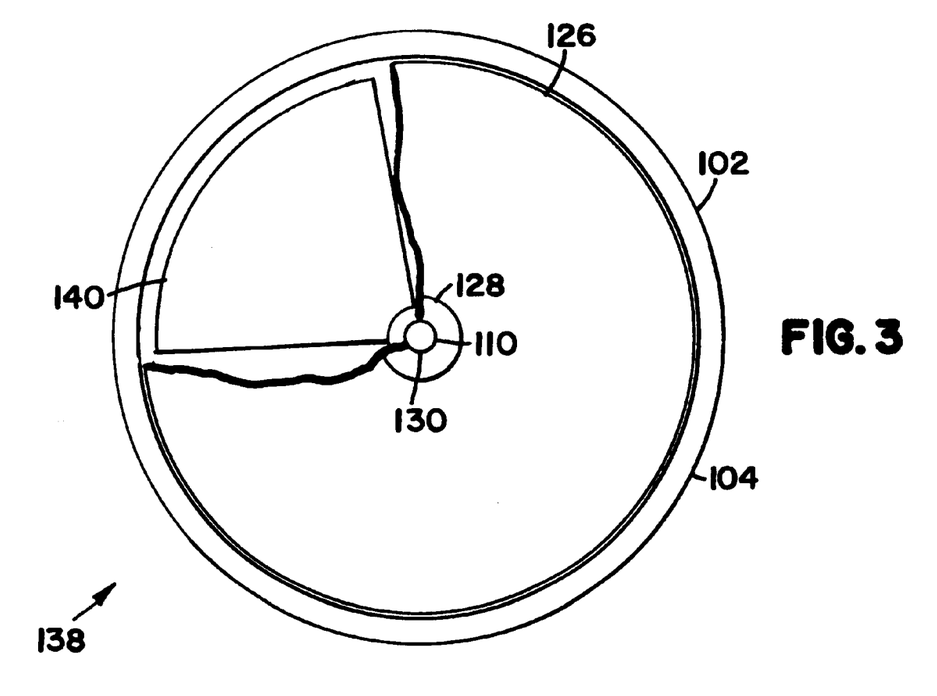
FIG. 3 is a fragmentary, side view of an alternative embodiment of the agent-delivery device show in FIG. 1 taken along line 3-3.

FIG. 3 shows another embodiment of an agent-delivery device, generally shown as 138, and similar to agent-delivery device 102. Agent-delivery device 138 includes the cap 102 having inner surface 106, reservoir 126, and probe 110. A delivery electrode 140 is pie-shaped and extends over only a limited portion of the inner surface 106 and the probe 110. This electrode configuration is advantageous because the caregiver can use the agent-delivery device to target a specific portion of the cervix. Other sizes, shapes, and positions of the delivery electrode 140 are possible. In yet other alternative embodiments, the size and shape of the reservoir 126 is also limited so that it covers only the delivery electrode 140.

Figure 4:
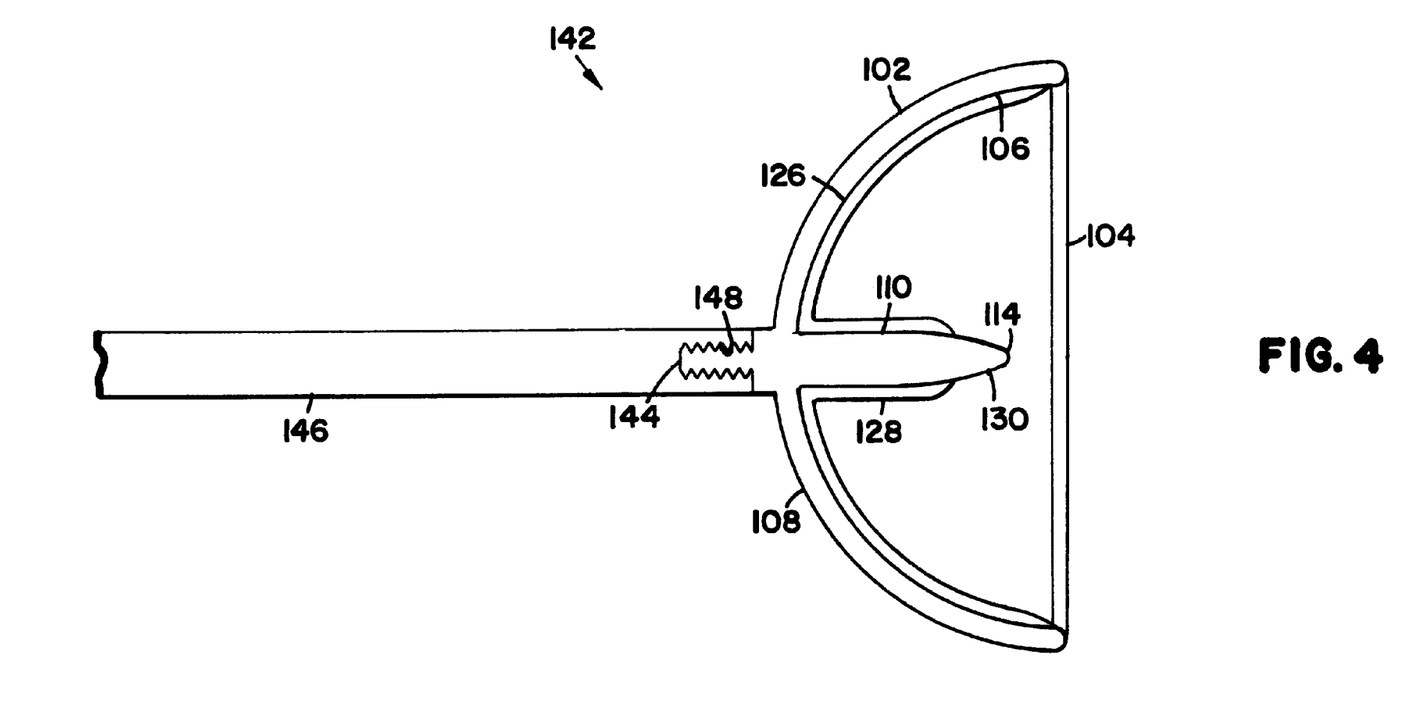
FIG. 4 is a fragmentary, cross-sectional view of an alternative embodiment of the agent-delivery device shown in FIG. 1.

FIG. 4 shows yet another alternative embodiment of an agent-delivery device, generally shown as 142, and similar to the agent-delivery device 100. The agent-delivery device 142 includes a cap 102 with an inner surface 106, reservoir 126, and probe 110. A threaded stud 144 projects from an outer surface 108 of the cap 102. An elongated body 146 has a threaded hole 148 and is threaded to the stud 144. In use, the caregiver can introduce and position the agent-delivery device 142 using the elongated body 146. Once the agent-delivery device 142 is in a delivery position, the caregiver can detach the elongated body 146 from the stud 144 and remove it from the patient's body. The agent is then passively absorbed into the cervical tissue.

This configuration has several advantages. For example, detaching the elongated body 146 will make the agent-delivery device 142 less intrusive and more comfortable for long-term delivery. Additionally, there are not wires or power supplies that a patient must secure to her body and conceal under clothing. As a result, the patient can move about more freely, which is important for long-term therapies.

An alternative configuration of the drug-delivery device 142 includes electrodes for iontophoretically transporting the agent from the reservoir 126 to the cervical tissue. In another alternative configuration, the detachable elongated body 146 defines a delivery lumen so that the reservoir 126 can be loaded after the cap 102 and probe 110 are placed in a delivery position. Additionally, the caregiver can reattach the elongated body 146 and then reload the reservoir 126 by injecting agent through the delivery lumen.

Figure 5:
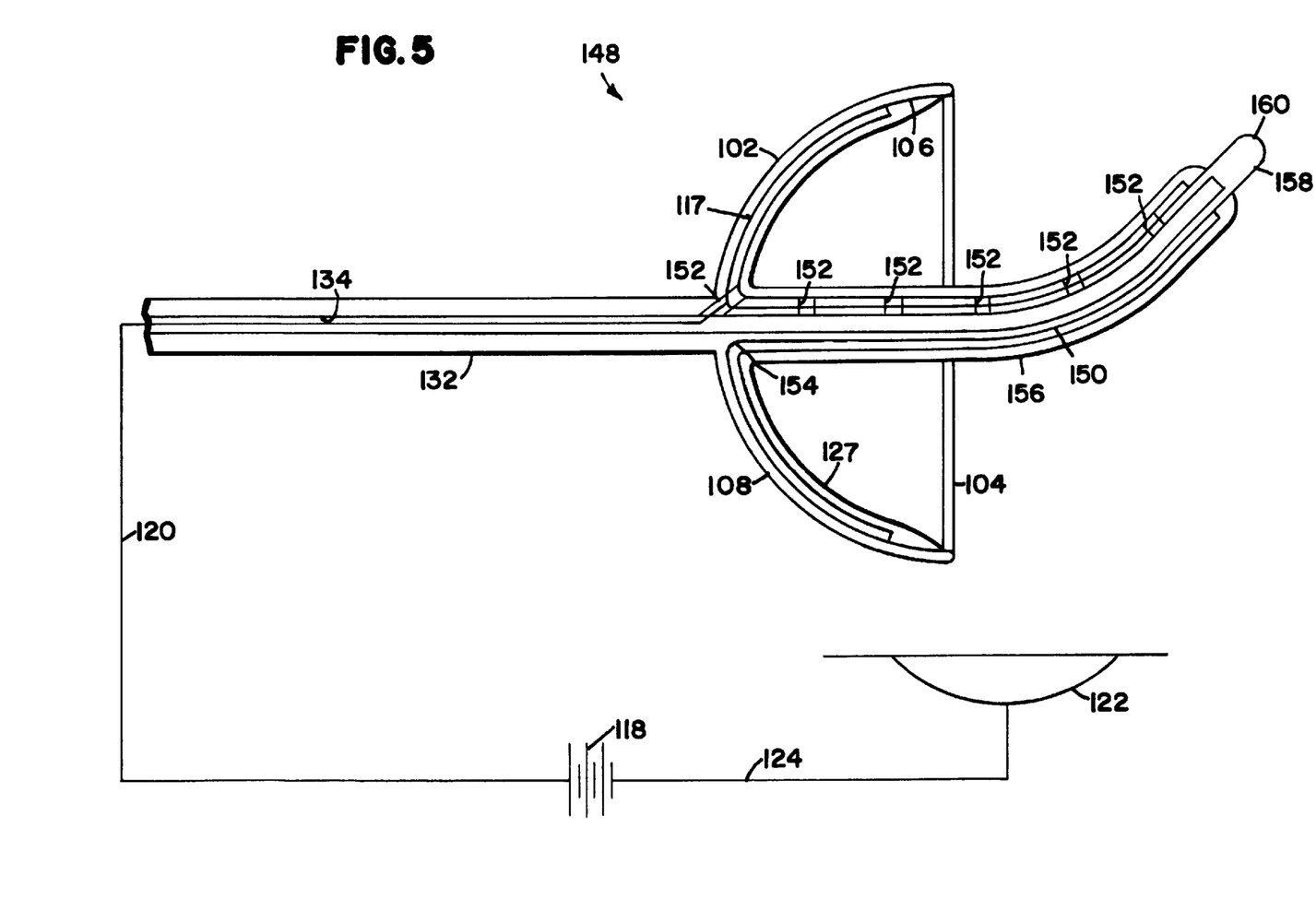
FIG. 5 is a fragmentary, cross-sectional view of another alternative embodiment of the agent-delivery device shown in FIG. 1.

FIG. 5 illustrates yet another alternative embodiment. An agent-delivery device, generally shown as 148, is similar to the agent-delivery device 100 and includes the cap 102 having inner surface 106, elongated body 132 having the delivery lumen 134, return electrode 122, and power supply 118. An elongated probe 150 extends outward from inner surface 106. The elongated probe 150 is sized to extend into the patient's uterine cavity when the cap 102 engages the cervix and is curved along its length to conform to the natural shape of the uterine cavity. In an alternative configuration, the elongated probe 150 is straight. In yet another alternative configuration, the elongated probe 150 is flexible enough to conform to the natural shape of the patient's uterine cavity, but still rigid enough to be inserted through the patient's cervical canal.

A delivery electrode 117 and a reservoir 127 extend along both the inner surface 106 of the cap 102 and the surface of the elongated probe 150. The reservoir 127 covers substantially all of the delivery electrode 117 to prevent direct contact between the electrode 117 and tissue in the patient's body. The delivery electrode 117 and reservoir 127 can have a variety of compositions and configurations as described herein. The delivery lumen 134 extends through substantially the entire length of the elongated probe 150. A plurality of delivery ports 152 provide fluid communication from the delivery lumen 134 to the uterine cavity. This configuration enables iontophoretic delivery of the agent to both the cervix and the uterine wall.

The elongated probe 150 has a base 154, delivery portion 156, an introducer portion 158, and a distal tip 160. The introducer portion 158 is tapered and is adjacent to the distal tip 160. In one possible configuration of the agent-delivery device 148, the length of the elongated probe 150 from the base 154 of the elongated probe 150 to the distal tip 160 is between about 4 cm and about 8 cm. The length of the introducer portion 158 is between about 1 cm and about 2 cm. The overall diameter of the elongated probe 150, including that portion of the reservoir 127 that extends along the probe 150, is set so that the probe 150 will transverse the cervical canal so that there is uniform contact between the probe 150 and cervical tissue. At the same time, the elongated probe 150 should not dilate the cervical tissue to the extent that it causes trauma, causes discomfort, or induces contractions. In one possible configuration, the diameter of the elongated probe 150 is between about 2 mm and about 5 mm. In an alternative embodiment, for example, the diameter of the probe 150 is large enough to dilate the cervical canal.

In an alternative configuration, the reservoir 127 is only along the inner surface 106 of the cap 102 and does not extend along the elongated probe 150. The portion of the delivery electrode 117 that extends along the elongated probe 150 is then covered with a sheath (not shown) that is either naturally conductive or conductive when it becomes wetted. The sheath prevents direct contact between the portion of the delivery electrode 117 that extends along the probe 150 and tissue in the patient's body. Because the uterine cavity itself acts as a reservoir when this embodiment is used, the sheath does not need to be made from a material that can retain or hold the agent.

Alternative configurations of the electrodes are also possible. In one such configuration, the delivery electrode 117 is operably connected to the elongated probe 150. There is no electrode mounted to the inner surface of the cap 102. These configurations may not include a reservoir 127, but still have a protective sheath covering the delivery electrode 117. There might also be a foam or gel on the inner surface 106 of the cap 102 to promote a fluid-tight seal against the vaginal surface of the cervix. In another possible configuration, the delivery electrode 117 is positioned within the delivery lumen 134. If the reservoir 127 is used, it still may be loaded with an agent, which then will be passively absorbed into the cervical tissue.

In use, the agent-delivery device 148 is positioned in the patient such that the cap 102 engages the patient's cervix and the elongated probe 150 extends into the patient's uterine cavity. An agent is then injected through the delivery lumen 134 until the reservoir 127 is loaded and the uterine cavity is substantially filled with agent. In order to ensure an even delivery of agent throughout the entire uterine wall, including the upper areas of tissue, the uterine cavity should be completely filled.

Once the uterine cavity is filled, the delivery and return electrodes 117 and 122 are energized. As a result, agent is iontophoretically transported into the patient's cervix and uterine wall. Again, the electrical current can be gradually increased and waveform can be varied. The cap 102 prevents fluid from leaking through the cervical canal.

EXPERIMENT

Two identical experiments compared iontophoretic delivery of an anesthetic into the uterine wall with passive delivery of the anesthetic into the uterine wall. Each experiment was conducted using segments of porcine uteri. In the first experiment, there were three trials of iontophoretic delivery using fresh segments of porcine uteri from the first pig and three trials of passive delivery using fresh segments of porcine uteri from the first pig. This procedure was repeated in the second experiment using segments of porcine uteri from the second pig. The weight of the pig for the first experiment was 110 lbs., and the weight of the pig for the second experiment was 120 lbs.

When running each trial for both the first and second experiments, the segment of porcine uterus was placed between two half diffusion cells, a donor cell and a receptor cell. The donor cell was filled with a 4% lidocaine solution. The receptor cell was filled with isotonic saline. After the experiment was complete, a tissue sample was taken from each segment of porcine uterus for lidocaine quantification. The tissue samples were analyzed using high pressure liquid chromatography (HPLC).

For the active delivery trials in each experiment, a donor or delivery electrode (anode) of Ag was placed in the donor cell and a receptor or return electrode (cathode) of AgCl was placed in the receptor cell. A 1 mA current was then conducted between the donor and receptor electrodes for 20 minutes. For the passive delivery trials in each experiment, the segments of porcine uteri were left in the diffusion cell opening between the donor solution and the receptor solution for 20 minutes.

The results for each experiment are as follows, where the data for the active trials area under the headings A1, A2, and A3. The data for the passive trials area under the headings P1, P2, and P3.

| | Experiment #1 Amount of lidocaine in each sample of tissue. | | | | | |
|---|---|---|---|---|---|---|
| | A1 | A2 | A3 | P1 | P2 | P3 |
| Mass of tissue (g) | 0.120 | 0.129 | 0.134 | 0.156 | 0.119 | 0.164 |
| $\mu$g/mL of lidocaine | 120.9 | 120.0 | 98.9 | 26.4 | 19.1 | 34.4 |
| Total $\mu$g in tissue | 604.6 | 600.2 | 494.6 | 131.8 | 95.5 | 172.1 |
| $\mu$g/g of tissue | 5050.8 | 4667.1 | 3694.6 | 847.6 | 801.6 | 1051.5 |

| | Experiment #2 Amount of lidocaine in each sample of tissue. | | | | | |
|---|---|---|---|---|---|---|
| | A1 | A2 | A3 | P1 | P2 | P3 |
| Mass of tissue (g) | 0.066 | 0.083 | 0.076 | 0.082 | 0.090 | 0.094 |
| $\mu$g/mL of lidocaine | 140.5 | 161.6 | 156.2 | 40.8 | 49.9 | 99.6 |
| Total $\mu$g/g in tissue | 702.3 | 808.2 | 781.1 | 203.9 | 249.2 | 498.0 |
| $\mu$g/g of tissue | 10592.3 | 9737.7 | 10318.0 | 2490.1 | 2757.2 | 5280.9 |

In the first experiment active delivery resulted in an average of 4471 ug of lidocaine/g of tissue and passive delivery resulted in an average of 900 ug of lidocaine/g of tissue. In the second experiment active delivery resulted in an average of 10216 ug of lidocaine/g of tissue and passive delivery resulted in an average of 3509 ug of lidocaine/g of tissue.

In an alternative method, the caregiver can fill the uterine cavity with a volume of fluid that is sufficient to pressurize the fluid and insufflate the fallopian tubes. The agent then can be passively absorbed through the wall of the fallopian tubes. Alternatively, an iontophoretic current can be used to actively transport the agent from the interior of the fallopian tubes into the wall of the fallopian tube and surrounding tissue. Iontophoresis through the wall of the fallopian tubes can be enhanced by inserting an electrode element hysteroscopically into the fallopian tubes. In one possible configuration, the electrode element consists of a wire that is coated with a lubricious and electrically conductive material that physically isolates the electrode from the wall of the fallopian tube.

Figure 6:
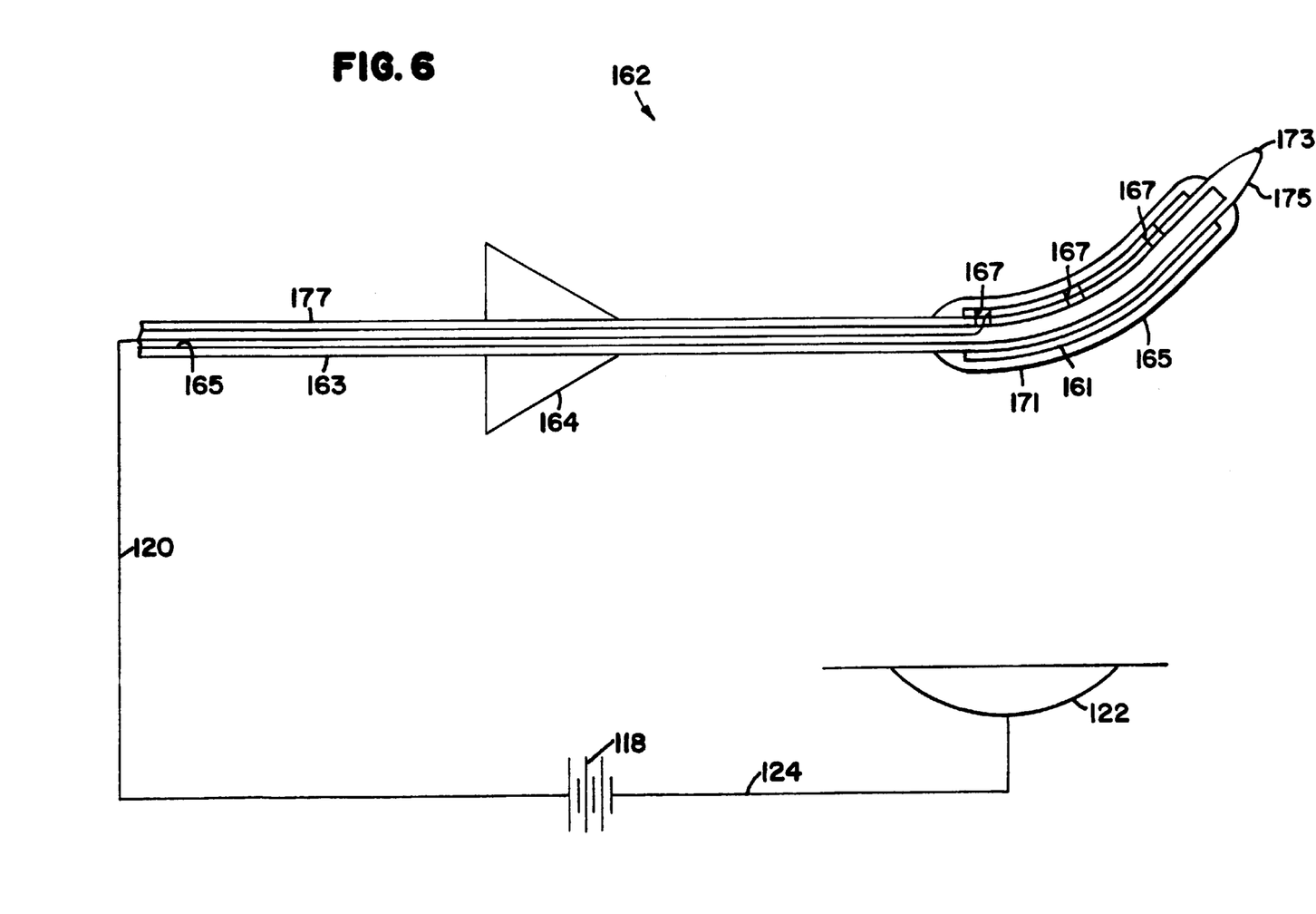
FIG. 6 is a fragmentary, cross-sectional view of yet another alternative embodiment of the agent-delivery device shown in FIG. 1.

FIG. 6 is an alternative embodiment of the agent-delivery device, generally shown as 162, and similar to agent-delivery device 148. Agent-delivery device 162 includes an elongated body 163 that defines a delivery lumen 166 and ports 167 that are in fluid communication with the delivery lumen 166. The elongated body 163 has a delivery portion 171, a proximal portion 177, and an introducer portion 175 at the distal tip 173. A delivery electrode 161 is mounted along substantially the entire length of the delivery portion 171 and is covered with a sheath 165 that is either naturally conductive or conductive when wetted. The agent-delivery device 162 also includes a return electrode 122, power supply 118, and first and second leads 120 and 124.

The agent-delivery device 162 does not include a cap. Rather, a plug 164 is operably connected to the elongated body 163 and positioned so that the delivery portion 171 is between the plug 164 and the distal tip 173. The plug 164 has a generally conical shape and is sized and oriented to be partially inserted into the patient's cervical canal. The shape and orientation of the plug 164 provides a substantially even and uniform fit between the surface of the cervical canal and the outer surface of the plug 164, which promotes agent retention within the targeted area. In one possible configuration, the plug 164 is in a fixed position. In this embodiment, the distance between the plug 164 and the distal tip 173 of the elongated body 163 is between about 4 cm and about 8 cm. In an alternative configuration, the plug 164 slidably engages the elongated body 163.

In one possible configuration, the plug 164 has a maximum diameter of about 1.0 cm to about 1.5 cm, a minimum diameter of about 2 mm to about 5 mm, and a length of about 1.5 cm to about 3 cm. The plug 164 is made of a biologically compatible material. Examples include, polyethylene, silicone, and polyurethane. Additionally, the plug 164 can include an electrode or reservoir similar to the cap 102, which was described above.

In use, the agent-delivery device 162 is positioned in the patient such that the delivery portion of the elongated body 163 extends into the uterine cavity and the plug 164 engages the cervical canal. Substantially all of the delivery portion 171 is located in the uterine cavity when the agent-delivery device 162 is in the delivery position. An agent is injected through the delivery lumen 165 until the uterine cavity is completely filled. The return electrode 122 is attached to the patient's skin. When the uterine cavity is filled, the delivery and return electrodes 161 and 122 are energized, and agent is iontophoretically transported into the patient's uterine wall. In an alternative method, the caregiver can deliver the agent to the fallopian tubes as described above.

Figure 7:
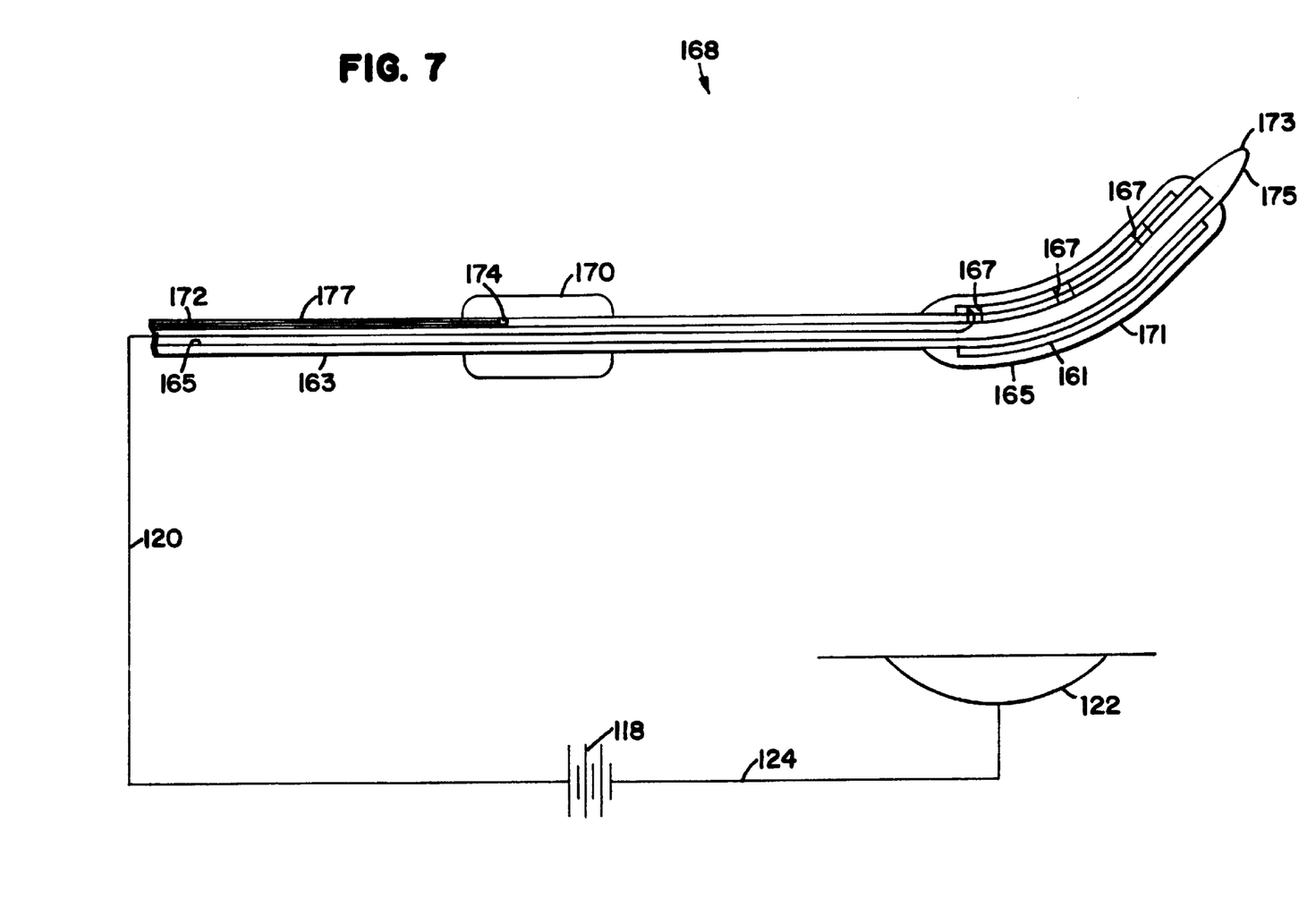
FIG. 7 is a fragmentary, cross-sectional view of yet another alternative embodiment of the agent-delivery device shown in FIG. 1.

FIG. 7 is an alternative embodiment of the agent-delivery device, generally shown as 168. Agent-delivery device 168 is similar to the agent-delivery device 162, but has an occlusion balloon 170 rather than a plug 164. Agent-delivery device 168 includes an elongated body 163 having a delivery portion 171; a proximal portion 177, and an introducer portion 175; delivery lumen 134, delivery and return electrodes 161 and 122; power supply 118; and sheath 165.

The delivery portion 171 of the elongated body 163 is between the occlusion balloon 170 and the distal tip 173.

In one possible embodiment, the distance between the occlusion balloon 170 and the distal tip 173 of the elongated body 163 is between about 4 cm and about 8 cm. The size of the occlusion balloon 170, when inflated, is configured to ensure a substantially even and uniform fit between the surface of the cervical canal and the outer surface of the occlusion balloon 170, which promotes agent retention within the uterine cavity. In another possible configuration, the occlusion balloon 170 is sized and shaped to be positioned within the vaginal canal and against the outer os of the cervix. The occlusion balloon 170 can be made from either elastic material or inelastic material. Examples of suitable elastic materials include latex, polyurethane, or silicone. Examples of suitable inelastic materials include polyethylene, polycarbonate, or PET.

The elongated body 163 defines an inflation lumen 172. The elongated body 163 also defines an inflation port 174 that provides fluid communication between the inflation lumen 172 and the occlusion balloon 170.

In an alternative embodiment, the occlusion balloon 170 is formed from a porous membrane such as a microporous membrane and inflated with an agent. Additionally, an electrode can be mounted on the elongated body and within the occlusion balloon 170. This configuration will enable or enhance delivery of an agent such as an anesthetic to the cervix. In another alternative embodiment, the occlusion balloon 170 has a metallic coating that forms an electrode and a reservoir much like the cap 102 described above.

Figure 8A:
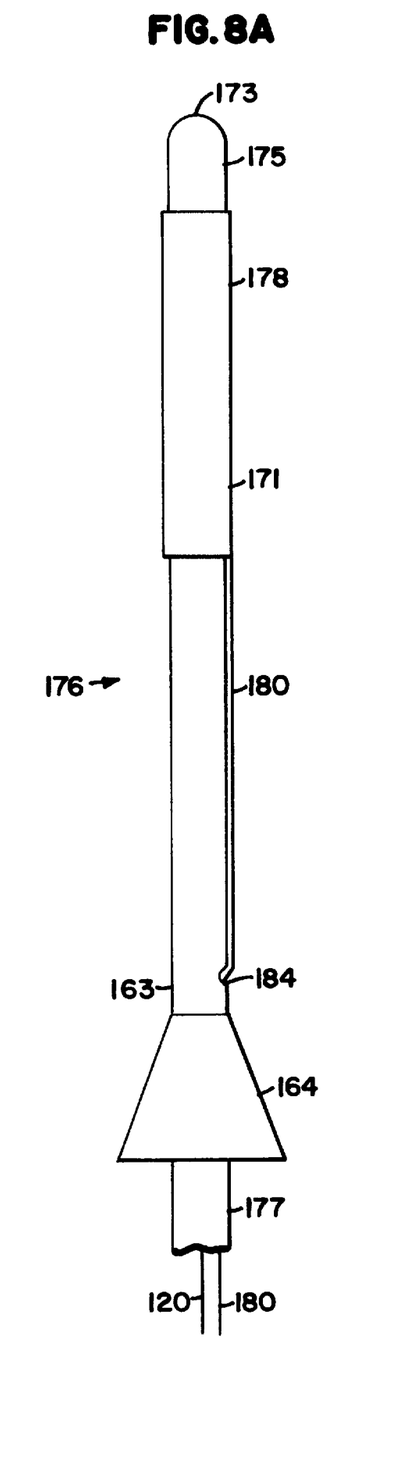
FIGS. 8A and 8B are fragmentary, elevational views of yet another alternative embodiment of the agent-delivery device shown in FIG. 1.
Figure 8B:
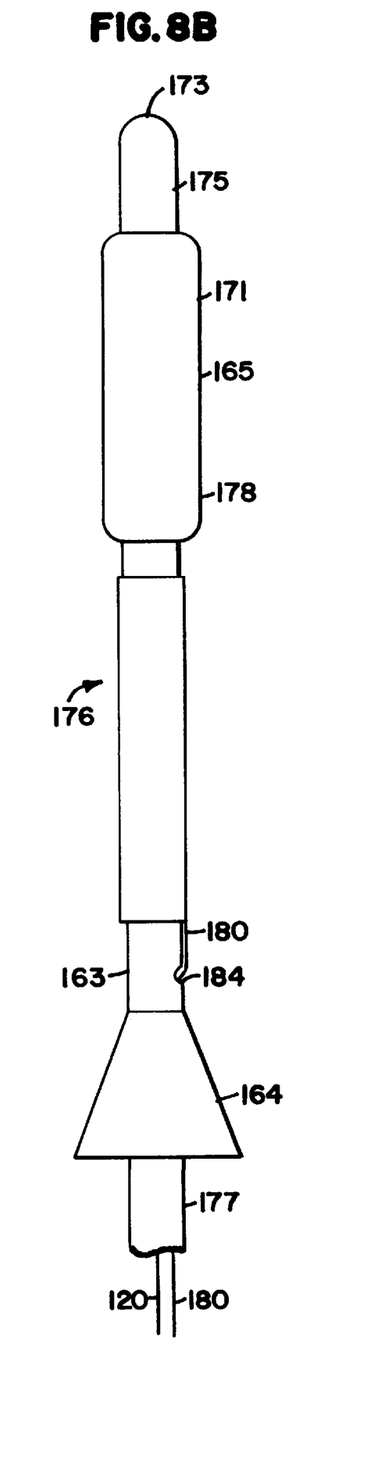

FIGS. 8A and 8B illustrate another alternative embodiment of the agent-delivery device, generally shown as 176, that is similar to agent-delivery device 162. Agent-delivery device 176 includes the lead 120; elongated body 163 having a delivery portion 171, a proximal portion 177, and an introducer portion 175; delivery lumen 165; plug 164; and sheath 165. The agent-delivery device 172 also includes a delivery electrode (not shown), return electrode (not shown), power supply and delivery lumen (not shown).

In one possible embodiment, the sheath 165 is formed from a compressible material such as an open-cell foam. The difficulty is that the sheath 165 may greatly increase the diameter of the agent-delivery device. Many women may feel discomfort or even pain if a medical device having a diameter greater than 3 mm is inserted through the cervical canal. Accordingly, referring to FIG. 8A, a jacket 178 is positioned around the sheath 165. The jacket 178 is formed from a biocompatible material such as polyurethane or polyethylene and is substantially inelastic. The jacket 178 holds the sheath 165 in a compressed state while the delivery portion 171 of the elongated body 163 is inserted through the cervical canal and placed in a delivery position. In one possible embodiment, the jacket 178 has a diameter of less than about 3 mm, but still slightly greater than the diameter of the elongated body 163. In other possible embodiments, the outer diameter of the jacket 178 is between about 2 mm and about 5 mm.

The jacket 178 is slidably engaged around the sheath 165, and the caregiver may pull the jacket 178 axially toward the proximal portion 177 of the elongated body 163 to expose the sheath 165 and hence the delivery electrode (not shown). In one possible embodiment, the inner surface of the jacket 178 has a lubricious coating. There are several possible mechanisms for pulling or withdrawing the jacket 178 to expose the sheath 165. One possible mechanism is a tether 180 that is attached to the proximal end 182 of the jacket 178. The tether 180 passes through a port 184 into a lumen (not shown) and then extends to the proximal end of the elongated body. The port 184 is spaced from the proximal end 182 of the jacket 178. The distance between the access port 184 to the lumen and the jacket 178 is about equal to or greater than the length of the jacket 178. In an alternative configuration, the tether 180 extends along the outer surface of the elongated body 163 to the proximal portion of the elongated body 163. In these configurations, the caregiver pulls on the tether 180 to withdraw the jacket 178.

In another alternative configuration, the jacket 178 is elongated and extends through the cervical canal when the agent-delivery device 176 is in a delivery position. In use, the caregiver grips the elongated jacket 178 itself to pull it toward the proximal portion 177 of the elongated body 163. This embodiment is useful if the plug 164 is replaced with an inflatable balloon, much like the balloon 170 described above. The jacket 178 could extend over the balloon, which would be exposed when the jacket 178 is withdrawn. In another possible embodiment, the plug 164 slidably engages the elongated body 163. The caregiver could cut away the jacket 178 and then slide the plug 164 forward until it engages the outer os of the cervix.

If the cervix is anesthetized, the agent-delivery device 176 can be removed without replacing the jacket 178 over the sheath 165. The anesthesia will minimize any discomfort or pain realized from the expanded sheath 165 passing through the cervical canal.

Figure 9:
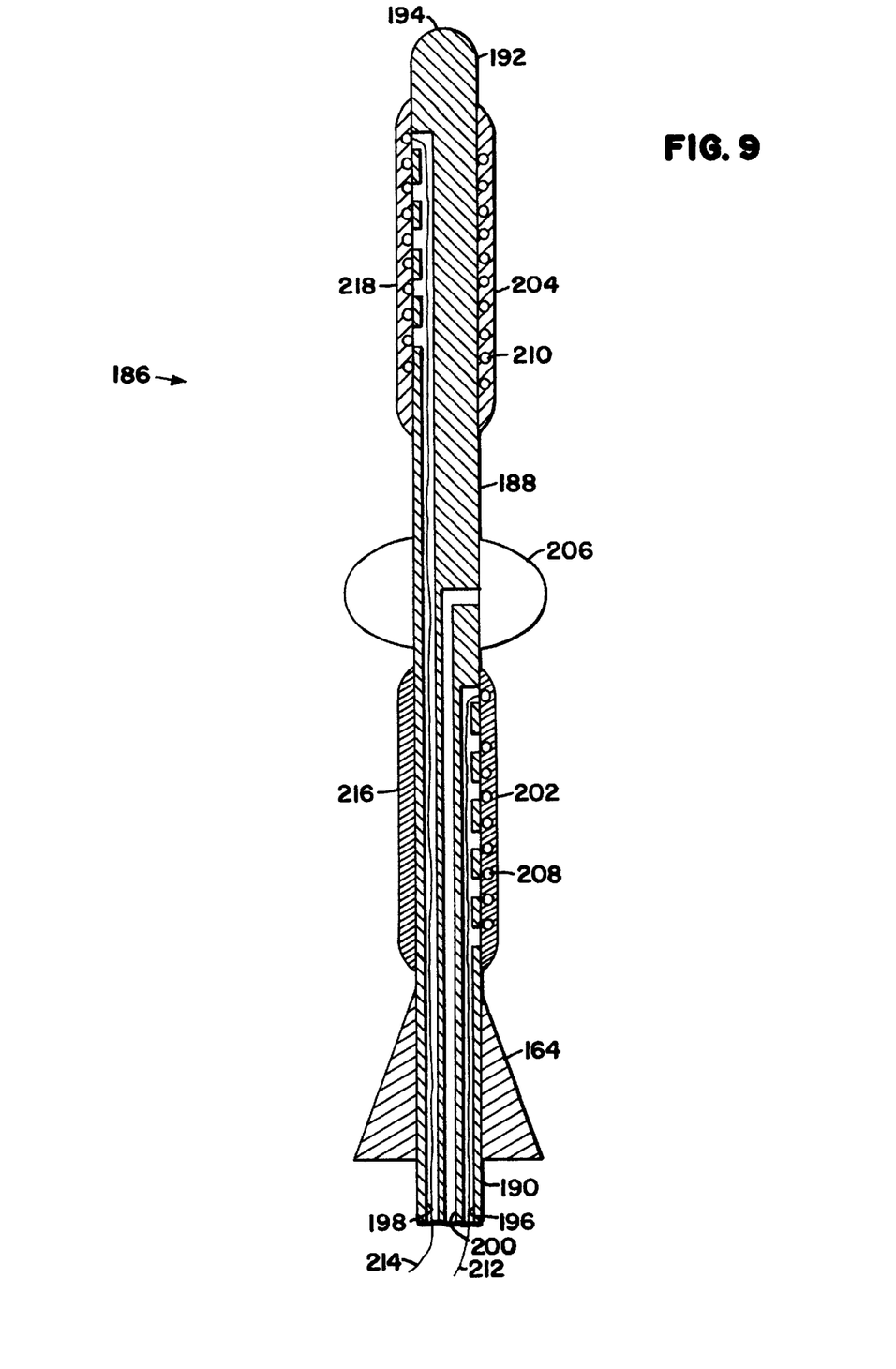
FIG. 9 is a fragmentary, cross-sectional view of yet another alternative embodiment of the agent-delivery device shown in FIG. 1.

FIG. 9 illustrates yet another alternative embodiment of the agent-delivery device, generally shown as 186, that allows controlled delivery of an agent into both the cervix and the uterine wall. The agent-delivery device 186 has a return electrode (not shown), power supply (not shown), and plug 164.

The agent-delivery device 186 has an elongated body 188 that includes a proximal portion 190, an introducer portion 192, and a distal tip 194. The elongated body 188 defines a first delivery lumen 196, a second delivery lumen 198, and an inflation lumen 200. The diameter of the elongated body 188 is between about 2 mm and about 5 mm. The elongated body 188 defines first and second delivery zones 202 and 204 positioned between the plug 164 and the distal tip 194 of the elongated body 188. The second delivery zone 204 is positioned between the first delivery zone 200 and the distal tip 194 of the elongated body 188. An occlusion balloon 206 is in fluid communication with the inflation lumen 200 and is positioned between the first and second delivery zones 202 and 204.

First and second delivery electrodes 208 and 210 extend around the elongated body 188. The first delivery electrode 208 is positioned in the first delivery zone 200, and the second delivery electrode 210 is positioned in the second delivery zone 202. A first lead 212 provides electrical communication between the first electrode 208 and the power supply, and the second lead 214 provides electrical communication between the second delivery electrode 210 and the power supply. The first and second leads 212 and 214 are connected to the power supply so that they have the same polarity and so that the caregiver can independently control. The first and second delivery electrodes 208 and 210.

A reservoir 216 is operably connected to and extends around the first delivery electrode 208. The reservoir 216 is in fluid communication with the first delivery lumen 196 and is positioned in the first delivery zone 200. A sheath 218 is operably connected to and extends around the second delivery electrode 210. The sheath 218 is positioned in the second delivery zone 202. An alternative configuration includes a jacket to minimize the diameter of the reservoir 216 and sheath 218 as the elongated body 188 is introduced into and passes through the cervical canal.

The first and second delivery electrodes 208 and 210 can have a variety of configurations such as a wire coiled around the elongated body 188 as shown or an electrically-conductive coating applied to the surface of the elongated body 188. In an alternative configuration, the first and second delivery electrodes 208 and 210 are positioned within the first and second delivery lumens 196 and 198, respectively.

The plug 164 is operably connected to the elongated body 188. The length of the elongated body 188 between the distal tip 194 and the plug 164 is between about 4 cm and about 8 cm. In an alternative configuration, the plug 164 is replaced with a second occlusion balloon similar to the occlusion balloon 170 described above. In yet another possible embodiment, the plug 164 is replaced with a cervical cap similar to the cap 102 described above. In this configuration, the first delivery electrode 208 and reservoir 216 can extend along the inner surface of the cap as described in more detail above.

In use, the elongated body 188 is passed through the cervical canal until the occlusion balloon 206 enters the uterine cavity. The occlusion balloon 206 is then inflated and retrograde tension is applied to the elongated body 188, which seats the occlusion balloon 206 against tissue adjacent to the internal cervical os. The occlusion balloon 206 substantially isolates the cervical canal from the uterine cavity. The caregiver places the plug 164 into engagement with the external cervical os.

The caregiver loads the reservoir 216 by injecting agent through the first delivery lumen 196. The caregiver can load the reservoir 216 either before or after the agent-delivery device 186 is placed into a delivery position. The caregiver also injects agent through the second delivery lumen 198 and floods the uterine cavity. The caregiver then controls the power supply to pass an electrical current from the first and second delivery electrodes 208 and 210 to the return electrode. The caregiver can independently control the voltage of each delivery electrode 208 and 210 and hence the current passing through each delivery electrode 208 and 210. For example, the caregiver might pass 5 mA through the first delivery electrode 208 in the cervical canal and only 1 mA through the second delivery electrode 210 in the uterine cavity.

This independent control is advantageous because the stratified squamous epithelium of the cervix is much more resistant, and less pervious, to the penetration of an agent than the endometrium that lines the uterine wall. Furthermore, some of the agent in the uterine cavity will be naturally absorbed through the endometrium into the uterine wall. The caregiver can independently control the electrical current in each delivery zone in order to optimize efficiency of the delivery. The caregiver can also deliver an ionized solutions having different agent concentrations, or even different agents, to the reservoir and the uterine cavity.

Although the description of the preferred embodiment and method have been quite specific, it is contemplated that various modifications could be made without deviating from the spirit of the present invention. Accordingly, it is intended that the scope of the present invention be dictated by the appended claims, rather than by the description of the preferred embodiment and method.

The claimed invention is:

1. A method of locally anesthetizing tissue in a reproductive tract, the reproductive track having a uterus defining a uterine cavity and an exocervix having an outer surface and an inner surface defining a cervical canal, the method comprising:

providing an agent-delivery device, the agent delivery device having a probe and a cervical cap connected to the probe, the probe defining a lumen;

inserting a probe through the cervical canal so that the lumen is in fluid communication with the uterine cavity;

placing the cervical cap in a position opposing the outer surface of the exocervix;

flooding the uterine cavity with the local anesthetic, flooding the uterine cavity including injecting agent through the lumen; and supplying the local anesthetic between the cervical cap and the outer surface of the exocervi.

2. The method of claim 1 wherein:

the cervical cap defines an inner surface and includes a reservoir material lining at least a portion of the inner surface;

placing the cervical cap in a position opposing the outer surface of the exocervix includes placing the reservoir material against the outer surface of the exocervix; and supplying the local anesthetic between the cervical cap and the outer surface of the exocervi includes loading the reservoir material with the local anesthetic.

3. The method of claim 2 wherein loading the reservoir material with the local anesthetic is performed before placing the reservoir material against the outer surface of the exocervix.

4. The method of claim 1 wherein the local anesthetic is selected from the group consisting essentially of lidocaine, carbocaine, bupivacaine, and ropivacaine.

5. The method of claim 1 wherein:

the cervical cap is formed with a pliable material; and placing the cervical cap in a position opposing the outer surface of the exocervix includes generally conforming the cervical cap to the outer surface of the exocervix.

6. The method of claim 1 further comprising creating a seal between tissue forming the outer surface of the exocervix and the cervical cap.

7. The method of claim 1 wherein:

the uterine cavity is curved; and inserting a probe through the cervical canal includes positioning at least a portion of the probe within the uterine cavity and aligning the probe to conform to the curve of the uterine cavity.

8. The method of claim 7 wherein:

the probe is formed from a pliable material; and aligning the probe to conform to the curve of the uterine cavity includes bending the probe.

9. The method of claim 1 wherein first and second electrodes are in electrical communication with a power supply and the first electrode is connected to the agent delivery device, the method further comprising:

positioning the first electrode within the reproductive tract;

positioning the second electrode against the outer surface of the patient's body; and conducting electrical current between the first and second electrodes, thereby iontophoretically transporting the local anesthetic into tissue of the patient's cervix and uterine wall.

10. A method of locally delivering an agent to tissue in a reproductive tract, the reproductive track having a uterus defining a uterine cavity and an exocervix having an outer surface and an inner surface defining a cervical canal, the method comprising:

providing an agent-delivery device, the agent delivery device having a probe and a cervical cap connected to the probe, the probe defining a lumen;

inserting a probe through the cervical canal so that the lumen is in fluid communication with the uterine cavity;

placing the cervical cap in a position opposing the outer surface of the exocervix;

selecting an agent to deliver to the reproductive tract;

flooding the uterine cavity with the agent, flooding the uterine cavity including injecting agent through the lumen; and supplying the agent between the cervical cap and the outer surface of the cervical surface.

11. The method of claim 10 wherein selecting an agent to deliver to the reproductive tract includes selecting an agent selected from the group consisting essentially of: dyes, fixatives, local anesthetics, cytotoxic agents, chemotherapeutic agents, photosensitive agents, antiviral agents, adjuvants, and penetration enhancers.

12. The method of claim 11 wherein:

the cervical cap defines an inner surface and includes a reservoir material lining at least a portion of the inner surface;

placing the cervical cap in a position opposing the outer surface of the exocervix includes placing the reservoir material against the outer surface of the exocervix; and supplying agent between the cervical cap and the outer surface of the cervical surface includes loading the reservoir material with agent.

13. The method of claim 11 wherein:

the uterine cavity is curved; and inserting a probe through the cervical canal includes positioning at least a portion of the probe within the uterine cavity and aligning the probe to conform to the curve of the uterine cavity.

14. The method of claim 11 wherein first and second electrodes are in electrical communication with a power supply and the first electrode is connected to the agent delivery device, the method further comprising:

positioning the first electrode within the reproductive tract;

positioning the second electrode against the outer surface of the patient's body; and conducting electrical current between the first and second electrodes, thereby iontophoretically transporting agent into tissue of the patient's cervix and uterine wall.

* * * * *